United States Patent
Kuhn

(10) Patent No.: US 10,542,921 B2
(45) Date of Patent: Jan. 28, 2020

(54) HERMETICALLY-SEALED PACKAGE AND METHOD OF FORMING SAME

(71) Applicant: Medtronic, Inc., Minneapolis, MN (US)

(72) Inventor: Jonathan L Kuhn, Ham Lake, MN (US)

(73) Assignee: Medtronic, Inc., Minneapolis ( * ) Notice: Subject to any disclaimer, the term of this patent is extended or adjusted under 35 U.S.C. 154(b) by 158 days.

(21) Appl. No.: 15/477,835

(22) Filed: Apr. 3, 2017

(65) Prior Publication Data
US 2018/0279924 A1 Oct. 4, 2018

(51) Int. Cl.
| A61B 5/1459 | (2006.01) |
| A61B 5/024 | (2006.01) |
| F21V 23/06 | (2006.01) |
| F21V 31/00 | (2006.01) |

(52) U.S. Cl.
CPC .......... *A61B 5/1459* (2013.01); *F21V 23/06* (2013.01); *F21V 31/005* (2013.01); *A61B 5/02427* (2013.01); *A61B 2562/12* (2013.01)

(58) Field of Classification Search
CPC . A61B 5/1455; A61B 5/1459; A61B 5/14551; A61B 5/14552; A61B 5/0261
See application file for complete search history.

(56) References Cited

U.S. PATENT DOCUMENTS

| 5,902,326 A | 5/1999 | Lessar et al. |
| 6,125,290 A | 9/2000 | Miesel |
| 6,125,291 A | 9/2000 | Miesel et al. |
| 6,134,459 A | 10/2000 | Roberts et al. |
| 6,583,445 B1 | 6/2003 | Reedy et al. |
| 6,586,776 B1 | 7/2003 | Liu |
| 7,653,434 B1 | 1/2010 | Turcott et al. |
| 8,090,432 B2 | 1/2012 | Cinbis et al. |
| 8,170,636 B2 | 5/2012 | Cinbis |
| 8,216,134 B2 | 7/2012 | Ries et al. |
| 8,275,432 B2 | 9/2012 | Kuhn et al. |
| 8,275,435 B2 | 9/2012 | Kuhn et al. |
| 8,290,557 B2 | 10/2012 | Davis et al. |
| 8,320,984 B2 | 11/2012 | Kuhn et al. |
| 8,346,332 B2 | 1/2013 | Kuhn et al. |
| 8,352,008 B2 | 1/2013 | Kuhn et al. |
| 8,391,979 B2 | 3/2013 | Kuhn et al. |
| 8,406,836 B2 | 3/2013 | Kuhn et al. |

(Continued)

OTHER PUBLICATIONS

Day, John K. et al., Sealed Pacakage Including Electronic Device and Power Source, U.S. Appl. No. 15/299,941, filed Oct. 21, 2016, 38 pages.

(Continued)

*Primary Examiner* — Thaddeus B Cox

(57) ABSTRACT

Various embodiments of a hermetically-sealed package and a method of forming such package are disclosed. The package can include a housing having an inner surface and an outer surface, and a non-conductive substrate hermetically sealed to the housing. The package can also include a light source disposed on a first major surface of the substrate and adapted to emit light through the first and second major surfaces of the substrate, and a detector disposed on the first major surface of the substrate and adapted to detect the light emitted by the light source.

17 Claims, 8 Drawing Sheets

(56) References Cited

U.S. PATENT DOCUMENTS

| | | |
|---|---|---|
| 8,452,402 B2 | 5/2013 | Ecker et al. |
| 8,458,543 B2 | 6/2013 | Tung |
| 8,463,343 B2 | 6/2013 | Kuhn et al. |
| 8,463,345 B2 | 6/2013 | Kuhn et al. |
| 8,463,346 B2 | 6/2013 | Kuhn et al. |
| 8,489,164 B2 | 7/2013 | Kuhn |
| 8,489,168 B2 | 7/2013 | Kuhn et al. |
| 8,515,537 B2 | 8/2013 | Cinbis et al. |
| 8,521,245 B2 | 8/2013 | Kuhn |
| 8,548,543 B2 | 10/2013 | Cinbis et al. |
| 8,571,620 B2 | 10/2013 | Cinbis et al. |
| 8,577,436 B2 | 11/2013 | Baker, Jr. |
| 8,630,708 B2 | 1/2014 | Kuhn et al. |
| 8,634,890 B2 | 1/2014 | Kuhn et al. |
| 8,639,332 B2 | 1/2014 | Kuhn et al. |
| 8,664,756 B2 | 3/2014 | Boone et al. |
| 8,666,466 B2 | 3/2014 | Kuhn et al. |
| 8,781,547 B2 | 7/2014 | Kuhn |
| 8,795,595 B2 | 8/2014 | Shah |
| 8,918,171 B2 | 12/2014 | Kuhn et al. |
| 9,044,181 B2 | 6/2015 | Kuhn et al. |
| 9,126,049 B2 | 9/2015 | Kuhn et al. |
| 9,326,711 B2 | 5/2016 | Kracker et al. |
| 2007/0156085 A1 | 7/2007 | Schulhauser et al. |
| 2008/0208020 A1 | 8/2008 | Cinbis et al. |
| 2009/0076353 A1 | 3/2009 | Carpenter et al. |
| 2009/0156912 A1 | 6/2009 | Kuhn et al. |
| 2009/0156918 A1 | 6/2009 | Davis et al. |
| 2010/0022856 A1 | 1/2010 | Cinbis et al. |
| 2010/0030043 A1 | 2/2010 | Kuhn |
| 2010/0185262 A1 | 7/2010 | Kuhn et al. |
| 2010/0262208 A1 | 10/2010 | Parker |
| 2010/0317947 A1 | 12/2010 | Cinbis et al. |
| 2010/0318146 A1 | 12/2010 | Cinbis et al. |
| 2011/0066017 A1 | 3/2011 | Kuhn |
| 2013/0103124 A1 | 4/2013 | Imran |
| 2013/0334680 A1 | 12/2013 | Boone et al. |
| 2014/0368266 A1 | 12/2014 | Askarinya et al. |
| 2015/0321011 A1 | 11/2015 | Carney et al. |
| 2015/0321012 A1 | 11/2015 | Cinbis et al. |
| 2016/0185081 A1 | 6/2016 | Sandlin et al. |
| 2016/0345872 A1* | 12/2016 | Wasson ............... A61B 5/1459 |
| 2018/0279932 A1 | 10/2018 | Boone et al. |

OTHER PUBLICATIONS (PCT/US2018/025801) PCT Notification of Transmittal of the International Search Report and the Written Opinion of the International Searching Authority, dated Jul. 4, 2018, 12 pages.

* cited by examiner

HERMETICALLY-SEALED PACKAGE AND METHOD OF FORMING SAME

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators, and drug pumps, which include electronic circuitry and one or more power sources, require an enclosure or housing to contain and seal these elements within a body of a patient. Many of these IMDs include one or more electrical feedthrough assemblies to provide electrical connections between the elements contained within the housing and components of the IMD external to the housing, for example, one or more sensors, electrodes, and lead wires mounted on an exterior surface of the housing, or electrical contacts housed within a connector header, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically-sealed housing to contain electronic circuitry of the sensor and an electrical feedthrough assembly to provide electrical connection between one or more lead wires, which extend within the implantable lead body, and the contained circuitry.

IMDs for monitoring a physiological condition and/or delivering a therapy can include one or more physiological sensors. Such sensors can provide one or more signals related to one or more physiological conditions of a patient state. Examples of such IMDs include heart monitors, pacemakers, implantable cardioverter defibrillators (ICDs), myostimulators, neurological stimulators, drug delivery devices, insulin pumps, glucose monitors, etc.

Optical sensors may be employed in IMDs as physiological sensors configured to detect changes in light modulation by, for example, a body fluid or tissue measurement volume due to a change in a physiological condition in the body fluid or tissue. Such optical sensors can be used, for example, to detect changes in metabolite levels in the blood, such as oxygen saturation levels or glucose level, or changes in tissue perfusion. A typical optical sensor can include one or more light sources and one or more detectors that are adapted to detect light emitted by the light sources and modulated by, e.g., body fluid or tissue measurement volume.

Monitoring such physiological conditions provides useful diagnostic measures and may be used in managing therapies for treating a medical condition. For example, a decrease in blood oxygen saturation or in tissue perfusion may be associated with insufficient cardiac output or respiratory function. Thus, monitoring such conditions may allow an implantable medical device to respond to a decrease in oxygen saturation or tissue perfusion, for example, by delivering electrical stimulation therapies to the heart to restore a normal hemodynamic function.

SUMMARY

In general, the present disclosure provides various embodiments of a sealed package and a method of forming such package. The sealed package can include a housing and a substrate sealed to the housing. The package can also include one or more light sources and detectors disposed within the housing. In one or more embodiments, one or more of the light sources and one or more of the detectors can be disposed on a first major surface of the substrate that faces the interior of the housing. The sealed package can be implanted in any suitable location within the patient and utilized to detect a physiological condition of the patient. For example, the physiological condition can be detected by analyzing at least a portion of light emitted by the light source and modulated by scattering from tissue of the patient.

In one aspect, the present disclosure provides a hermetically-sealed package that includes a housing having an inner surface and an outer surface, and a non-conductive substrate hermetically sealed to the housing by a laser bond, where the substrate includes a first major surface and a second major surface. The package further includes a light source disposed on the first major surface of the substrate and adapted to emit light through the first and second major surfaces of the substrate, and a detector disposed on the first major surface of the substrate and adapted to detect the light emitted by the light source.

In another aspect, the present disclosure provides a method of forming a hermetically-sealed package that includes disposing a light source on a first major surface of a transparent substrate, disposing a detector on the first major surface of the transparent substrate, and hermetically sealing the transparent substrate to the housing. Hermetically sealing the transparent substrate to the housing includes laser bonding the first major surface of the substrate to the housing.

In another aspect, the present disclosure provides a method of forming a hermetically-sealed package. The method includes forming a recess in a major surface of a wafer, disposing a power source within the recess of the wafer, and disposing a light source on a first major surface of a transparent substrate. The method further includes disposing a detector on the first major surface of the transparent substrate, hermetically sealing the first major surface of the substrate to the wafer, and removing a portion of the wafer and substrate to form the hermetically-sealed package.

In another aspect, the present disclosure provides a method of detecting a physiological condition of a patient. The method includes disposing a hermetically-sealed package within a body of the patient. The hermetically-sealed package includes a housing having an inner surface and an outer surface, and a non-conductive substrate hermetically sealed to the housing by a laser bond, where the substrate includes a first major surface and a second major surface. The package further includes a light source disposed on the first major surface of the substrate, and a detector disposed on the first major surface of the substrate. The method further includes directing light from the light source such that it is incident upon one or both of tissue and an artery of the patient, detecting a portion of the emitted light that is scattered by one or both of the tissue and the artery of the patient utilizing the detector, and determining the physiological condition of the patient based upon a characteristic of the detected light.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
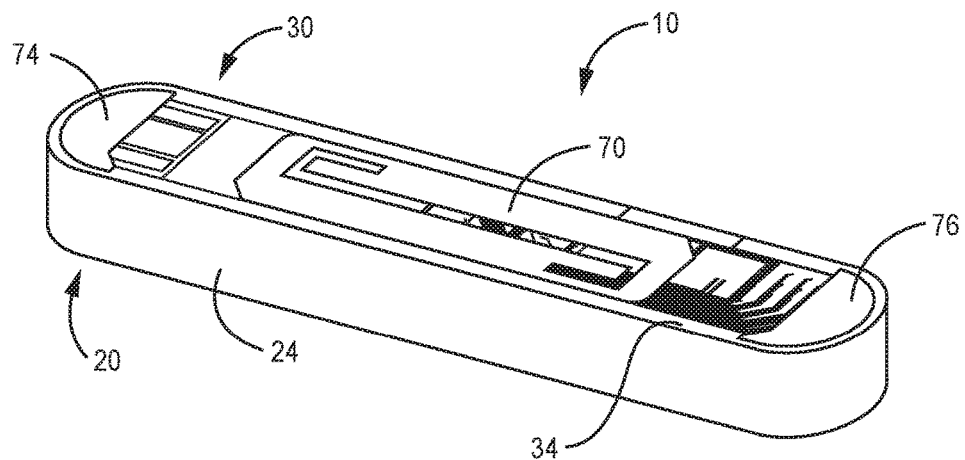
FIG. 1 is a schematic perspective view of one embodiment of a sealed package.

In general, the present disclosure provides various embodiments of a sealed package and a method of forming such package. The sealed package can include a housing and a substrate sealed to the housing. The package can also include one or more light sources and detectors disposed within the housing. In one or more embodiments, one or more of the light sources and one or more of the detectors can be disposed on a first major surface of the substrate that faces the interior of the housing. The sealed package can be implanted in any suitable location within the patient and utilized to detect a physiological condition of the patient. For example, the physiological condition can be detected by analyzing at least a portion of light emitted by the light source and modulated by scattering from tissue of the patient.

The various embodiments of sealed packages described herein can be utilized for remote patient diagnostics, monitoring, and treatment with any suitable system. For example, one or more embodiments of sealed packages described herein can include an implantable medical device or system disposed within the sealed package. In one or more embodiments, the sealed package can be electrically connected to an implantable medical device. Nearly any implantable medical device or system employing leads may be used in conjunction with the various embodiments of sealed packages described herein. Representative examples of implantable medical devices included in or utilized with the various embodiments of sealed packages described herein include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators, ventricular assist devices; or the like.

Recently, health care costs have dramatically risen in part from the increased incidence of chronic diseases such as heart failure, sleep apnea, and chronic obstructive pulmonary disease (COPD), and interactions of such. These chronic diseases are often managed in a cyclic response to symptoms, i.e., the patient becomes increasingly symptomatic, goes to the clinician, and the clinician diagnoses and treats the condition. Clinician visits, however, are expensive. Further, the cost to treat such patients increases significantly with worsening symptoms. On the other hand, prevention along with adequate warnings given to the patient can be much less expensive.

Currently, clinicians gather and assimilate a wealth of information to diagnose and manage patients. Such information can be gathered using lab work, in-office biomedical measurements, and direct observations and information from the patient. Oftentimes, a trial treatment can be prescribed, and the efficacy of such treatment can be confirmed by observing the various responses of the patient to the treatment.

Previous attempts at providing chronically implantable detection devices such as optical sensors have proven to be challenging because of the high cost, the large size, and the relatively large number of components needed to form such detection devices. One purpose of using optical sensors in such chronically implantable settings is to better guide existing therapies and reduce clinical burdens.

One or more embodiments of sealed packages described herein that include one or more sensors (e.g., optical sensors) can provide a low-cost mechanism for providing remote measurements of one or more physiological conditions of a patient. An exemplary embodiment of a sealed package can provide earlier indications that a patient is trending toward a worsening condition prior to becoming symptomatic. Further, one or more embodiments of sealed packages described herein can enable low-power subcutaneous optical sensing at reduced cost and size over prior solutions. Such packages can also provide remote monitoring of any desired physiological condition, e.g., arterial oxygen, under controlled and repeatable conditions that can be difficult and cumbersome to reliably monitor with typical external devices.

Figure 2:
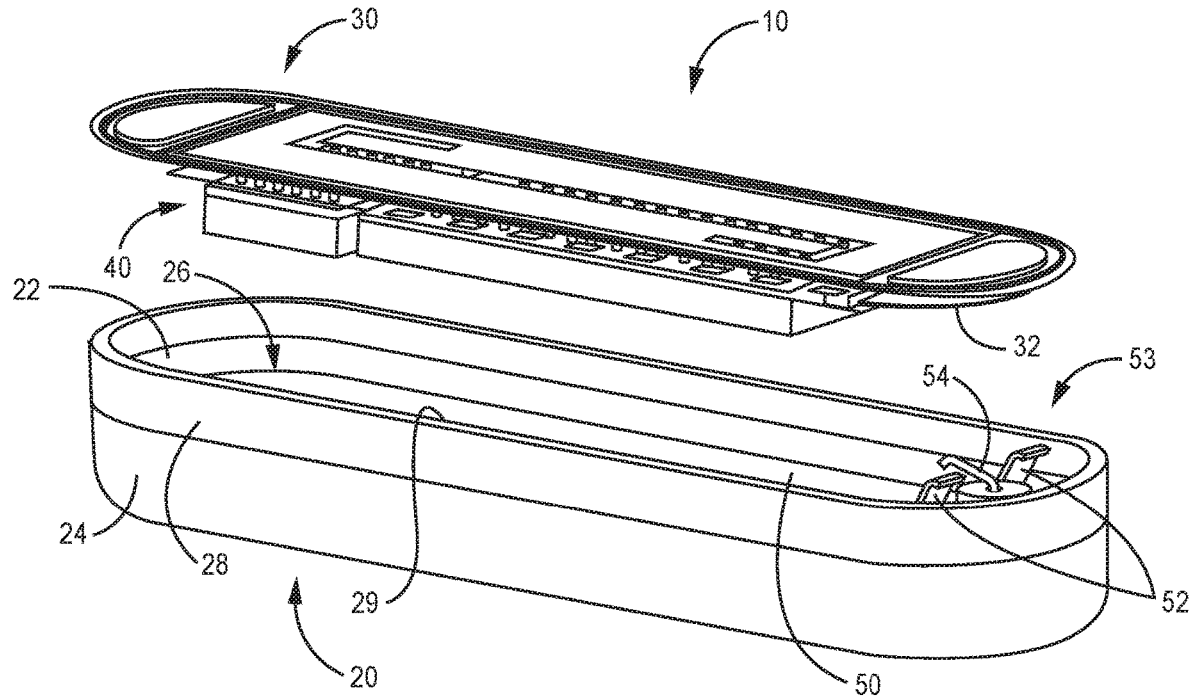
FIG. 2 is a schematic exploded view of the sealed package of FIG. 1.
Figure 3:
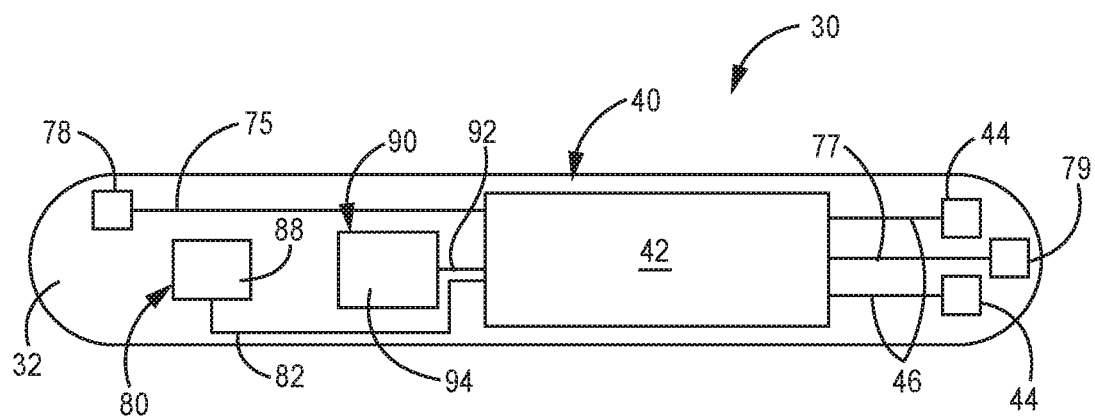
FIG. 3 is a schematic plan view of a first major surface of a substrate of the sealed package of FIG. 1.
Figure 4:
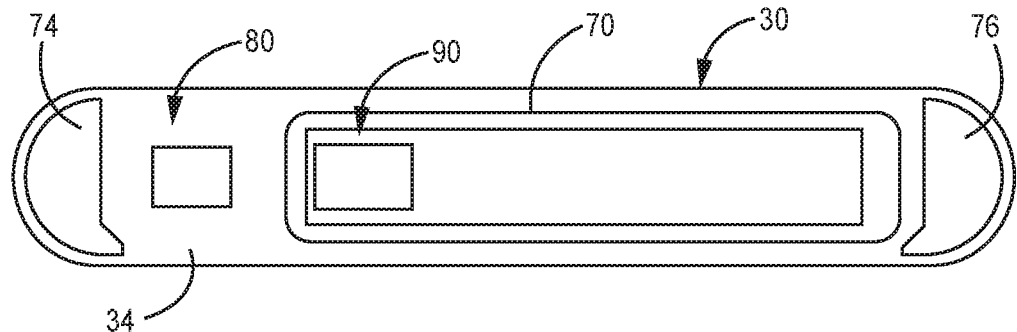
FIG. 4 is a schematic plan view of a second major surface of the substrate of the sealed package of FIG. 1.

FIGS. 1-5 are various schematic views of one embodiment of a sealed package 10. The package 10 includes a housing 20 and a substrate 30. The housing 20 includes an inner surface 22 and an outer surface 24. The substrate 30 can be a non-conductive substrate and includes a first major surface 32 and a second major surface 34. The package 10 can also include one or more electronic devices 40 disposed within the housing 10. For example, the electronic devices 40 can include a light source 80 (FIG. 3). In one or more embodiments, the light source 80 can be disposed on the first major surface 32 of the substrate 30. The light source 80 can be adapted to emit light through the first and second major surfaces 32, 34 of the substrate 30. The electronic devices 40 can further include a detector 90 (FIG. 3). In one or more embodiments, the detector 90 can be disposed on the first major surface 32 of the substrate 30. The detector 90 can be adapted to detect the light emitted by the light source 80. Together, the light source 80 and the detector 90 can, in one or more embodiments, provide an optical sensor.

The package 10 also includes a power source 50 that is disposed at least partially within the housing 20. In one or more embodiments, the power source 50 can be disposed within a cavity 26 of the housing 20. The power source 50 can include any suitable power source or sources as is further described herein.

The substrate 30 can be sealed to the housing 20. In one or more embodiments, the substrate 30 can be hermetically sealed to the housing 20. The substrate 30 can be sealed to the housing 30 using any suitable techniques or techniques. In one or more embodiments, the substrate 30 can be hermetically sealed to the housing 20 by a laser bond.

The housing 20 can include any suitable material or materials, e.g., metallic, polymeric, ceramic, or inorganic materials. In one or more embodiments, the housing 20 can include at least one of glass, quartz, silica, sapphire, silicon carbide, diamond, and gallium nitride. In one or more embodiments, the housing 20 can include at least one of copper, silver, titanium, niobium, zirconium, tantalum, stainless steel, platinum, and iridium. The housing 20 can include the same material or combination of materials as the substrate 30. In one or more embodiments, the housing 20 can include one or more materials that are different from the material or materials of the substrate 30. Further, in one or more embodiments, the housing 20 can include biocompatible materials such that the package 10 can be implanted within a patient's body. For example, one or more coatings or layers can be disposed on the outer surface 24 of the housing 20 that provide biocompatibility. In one or more embodiments, the housing 20 can be electrically conductive to provide a ground electrode for the package 10 as is known in the art. In one or more embodiments, the housing 20 can be nonconductive.

Further, the housing 20 can take any suitable shape or combination of shapes and can have any suitable dimensions. In one or more embodiments, the housing 20 takes a shape that forms the cavity 26 that can accommodate the power source 50 (including active material and power source electronics) and one or more electronic devices 40 as is further described herein.

Sealed to the housing 20 is the substrate 30. In one or more embodiments, the substrate 30 can be a non-conductive or insulative substrate such that the electronic devices 40 (including light source 80 and detector 90), optional external electrodes 74, 76, and any conductors or other devices disposed on the substrate can be electrically isolated if desired. The substrate 30 can include any suitable material or materials. In one or more embodiments, the substrate 30 can include at least one of glass, quartz, silica, sapphire, silicon carbide, diamond, and gallium nitride. As with the housing 20, the substrate 30 can include a biocompatible material. For example, the substrate 30 can include one or more coatings or layers that can provide biocompatibility.

In one or more embodiments, the substrate 30 can be a transparent substrate. As used herein, the phrase "transparent substrate" refers to a substrate that can transmit a given percentage of light incident thereon during use of laser bonding techniques described herein to preferentially heat only an outer surface of the substrate (e.g., first major surface 32 or second major surface 34 of substrate 30), and not an inner bulk of the substrate, and thereby create a bond that has a relatively greater strength than the bulk strength of the substrate. Further, the transparent substrate 30 can transmit light emitted by the light source 80 having any suitable wavelength or combinations of wavelengths. The substrate 30 can be substantially transparent at a desired wavelength or range of wavelengths. As used herein, the phrase "substantially transparent" means that the substrate 30 transmits greater than 50% of light incident on the substrate for a selected wavelength or range of wavelengths, assuming no reflection at the air-substrate boundaries. In one or more embodiments, the substrate 30 can be substantially transmissive to light having a wavelength of at least 200 nm. In one or more embodiments, the substrate 30 can be substantially transmissive to light having a wavelength of greater than 10,000 nm. In one or more embodiments, the substrate 30 can be substantially transmissive to light having a wavelength in a range of 200 nm to 10,000 nm. In one or more embodiments, the substrate 30 can be substantially transmissive to at least one of UV light, visible light, and IR light.

In one or more embodiments, at least a portion of the substrate 30 can be transparent such that the detector 90 disposed on the first major surface 32 can detect one or more external signals, e.g., from a patient, when the package 10 is disposed within the patient. In one or more embodiments, the at least a portion of the substrate 30 can be sufficiently transparent to enable transmission of all, or a sufficient magnitude, of the light that is incident on the substrate for reception by the detector 90 such that the received light can be processed to detect the external signal. In one or more embodiments, the substrate 30 can be opaque, and a through-hole can be formed through the substrate and filled with a transparent hermetic material such as glass to provide a transparent portion of the substrate.

The substrate 30 can include any suitable dimensions, e.g., thicknesses. Further, the substrate 30 can take any suitable shape or combinations of shapes. In one or more embodiments, the substrate 30 can take a shape or combination of shapes that is complementary to a shape of the housing 20 such that the substrate can be sealed to the housing and provide a low-profile shape for the sealed package 10. Further, the substrate 30 can be a single, unitary substrate or multiple substrates joined together.

Disposed on the first major surface 32 of the substrate 30 are the electronic devices 40. Although depicted as being disposed on the first major surface 32, one or more electronic devices 40 can be disposed on the second major surface 34, or one or more electronic devices can be disposed on both the first and second major surfaces. In one or more embodiments, one or more electronic devices 40 can be disposed within the housing 20 and not connected to the substrate 30. The electronic devices 40 can include any suitable circuit or component, e.g., capacitors, transistors, integrated circuits, including controllers and multiplexers, sensors, light sources, detectors, accelerometers, signal processors, etc.

Further, any suitable technique or combination of techniques can be utilized to dispose one or more electronic devices 40 on the substrate 30 and/or within the cavity 26 of the housing 20. In one or more embodiments, one or more electronic devices 40 can be formed on the first major surface 32 of the substrate 30. In one or more embodiments, one or more devices 40 can be formed separately and then attached to the first major surface 32. Any suitable technique or techniques can be utilized to attach the electronic devices 40 to the substrate 30, e.g., a bond can be formed between the electronic device and the first major surface 32 of the substrate.

The electronic devices 40 can include one or more light sources 80. The light source 80 can include any suitable light source or combination of light sources. For example, the light source 80 can include any electrical circuit component(s) capable of emitting light in response to an applied voltage or current, including, for example, light emitting diodes (LEDs), laser diodes, vertical cavity surface emitting lasers (VCSELs), organic LEDs printed directly on the surface, nano-emitters, etc. The light source 80 can be a cluster of one or more components that emit one or more discrete wavelengths, or broadband emitters spanning a large range of wavelengths.

Although depicted as including a single light source 80, the device 10 can include any suitable number of light sources as is further described herein. The light source 80 can include an emitting surface 88. Although depicted as having one emitting surface 88, the light source 80 can include two or more emitting surfaces.

The light source 80 can be a packaged light source. In one or more embodiments, the light source 80 can include a flip-chip type package. In one or more embodiments, the light source 80 can be a bare semiconductor die.

The light source 80 can be adapted to emit light of any suitable wavelength or wavelengths. In one or more embodiments, the light source 80 can emit at least one of infrared, near-infrared, visible, and UV light. In one or more embodiments, the light source 80 can emit visible light having a wavelength of at least 350 nm and no greater than 850 nm. The light source 80 can emit any suitable bandwidth of light. In one or more embodiments, the light source 80 can emit light in a narrow band, e.g., the light source is adapted to emit light having an emission profile no greater than 20 nm, 15 nm, 10 nm, or 5 nm full-width at half-maximum (FWHM). In one or more embodiments, a narrow band source can be paired with a broadband detector that is sensitive to all of the wavelengths emitted by the source. In one or more embodiments, a narrow-band source can be paired with a narrow-band detector. Further, in one or more embodiments, a narrow band source can be paired with two or more broadband detectors. For example, silicon detectors can be sensitive in the visible to near-infrared wavelength ranges (e.g., up to about 1000 nm), but gallium arsenide can be sensitive to longer infrared wavelengths (e.g., greater than 1000 nm).

In one or more embodiments, the light source 80 can include a broadband emitter that utilizes re-emission of phosphorous materials or combination of broadband FWHM LEDs, e.g., a 680 nm LED with greater than a 50 nm FWHM that spans into the 720 nm wavelength. In such embodiments, a single LED can provide emission at both 680 nm and 720 nm, paired with a detector 90 that can discriminate between these two wavelengths. Similarly, a second broadband FWHM light source 80 can be used at 800 nm that also spans 760 nm. In such embodiments, two broadband FWHM LEDs can span four wavelengths, e.g., 680, 720, 760, and 800 nm and can be paired with a detector 90 that can detect all four wavelengths. In such embodiments, the detector 90 can include a narrow band pass filter or filters to detect the emitted light.

In one or more embodiments, the light source 80 can be adapted to emit light in one or more pulses having any suitable pulse width and periodicity. Further, in one or more embodiments, the light source 80 may be pulsed in a sequential manner.

The light source 80 can have any suitable cone angle of emission. As used herein, the term "cone angle" refers to solid angle relative to a normal to the surface of the emitter. In one or more embodiments, the light source 80 can have a cone angle of no greater than 90 degrees, 80 degrees, 70 degrees, 60 degrees, 50 degrees, 40 degrees, 30 degrees, 20 degrees, 10 degrees, or 5 degrees. In one or more embodiments, the light source 80 can include one or more optical elements that can direct light through the substrate 30 to increase light source efficiency and to prevent light from leaking into the interior of the housing 20, thereby causing interference with other components disposed within the housing.

In general, the number of light sources 80 and corresponding emission wavelengths utilized in the packages described herein can be selected according to the requirements of a particular application and will depend on the physiological condition or conditions being monitored.

Figure 5:
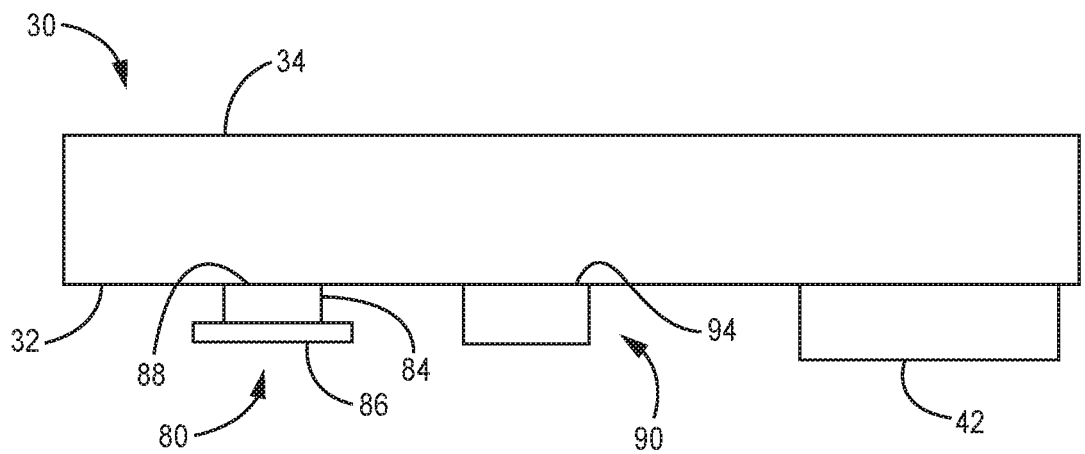
FIG. 5 is a schematic cross-section view of the substrate of the sealed package of FIG. 1.

The light source 80 can be disposed in any suitable location within the housing 20 of the device 10. In one or more embodiments, the light source 80 is disposed adjacent the first major surface 32 of the substrate 30. As used herein, the term "adjacent" means that an element or component is disposed closer to the first major surface 32 of the substrate 30 than to the power source 50 disposed within the housing 20. In one or more embodiments, the light source 80 can be disposed on the first major surface 32 of the substrate 30 as shown in FIG. 5 using any suitable technique or techniques. In such embodiments, an emitting surface 88 of the light source 80 can be connected to the first major surface 32 of the substrate 30 using any suitable technique. For example, in one or more embodiments, the emitting surface 88 can be disposed on the second major surface 32 of the substrate 30 using an optical coupling layer (not shown). Any suitable coupling layer can be utilized. In one or more embodiments, a refractive index of the optical coupling layer can be selected such that a substantial portion of the light emitted by the light source 80 is directed from the emitting surface 88 and into the substrate 30 without a substantial portion of the emitted light being reflected at a boundary between the emitting surface and the first major surface 32 of the substrate 30. In one or more embodiments, the optical coupling layer can include an optical adhesive.

The light source 80 can be electrically connected to one or more electronic devices 40 disposed on one or both of the first major surface 32 and second major surface 34 of the substrate 30 or within the housing 20 using any suitable technique or techniques. For example, the light source 80 can be electrically connected to a conductor 82 (FIG. 3) that is disposed on or within the substrate 30. The conductor 82 can electrically connect the light source 80 to a controller 42 of the electronic devices 40. Any suitable technique or techniques can be utilized to electrically connect the light source 80 to the conductor 82, e.g., bump bonding, solder reflow, conventional wire bonding, laser ribbon bonding, conductive epoxy bonding, etc.

The package 10 also includes the detector 90. The detector 90 includes a detecting surface 94 (FIG. 3). The detector 90 can include any suitable detector that is adapted to detect light emitted by the light source 80, e.g., one or more photodiodes, photoresistors or light dependent resistors, phototransistors, photovoltaic cells, charge-coupled devices, avalanche detectors, etc. In one or more embodiments, a light source 80 can also be utilized as a detector. Although depicted as including a single detector 90, the package 10 can include any suitable number of detectors as is further described herein.

The detector 90 can be adapted to detect any desired wavelength or wavelengths. In one or more embodiments, the detector 90 can detect one or more of infrared, near-infrared, visible, and UV light. In one or more embodiments, the detector 90 can detect visible light having a wavelength of at least 350 nm and no greater than 850 nm.

The detector 90 can be disposed in any suitable location within the housing 20 of the device 10 or outside of the housing (e.g., on the second major surface 34 of the substrate 30). In one or more embodiments, the detector 90 is disposed adjacent the first major surface 32 of the substrate 30. In one or more embodiments, the detector 90 can be disposed on the first major surface 32 of the substrate 30 using any suitable technique or techniques as shown in FIG. 5. In such embodiments, the detecting surface 94 can be connected to the first major surface 32 of the substrate 30 using any suitable technique. For example, in one or more embodiments, the detecting surface 94 can be disposed on the first major surface 32 of the substrate 30 using an optical coupling layer. Any suitable coupling layer can be utilized. In one or more embodiments, the optical coupling layer can include an optical adhesive. In one or more embodiments, the detector 90 can be electrically connected to an electrode disposed on a carrier. The detector 90 can also be wired bonded from the light source 80 to a second electrode on the carrier. The carrier can be designed such that the two electrodes are in a single plane. the carrier can then be bump-bonded to one or more conductors (e.g., conductor 92) disposed on the substrate 30.

The detector 90 can be electrically connected to one or more of the other electronic devices 40 disposed on one or both of the first major surface 32 and second major surface 34 of the substrate 30 or within the housing 20 using any suitable technique or techniques. For example, the detector 90 can be electrically connected to a conductor 92 that is disposed on or within the substrate 30. In one or more embodiments, the conductor 92 can electrically connect the detector 90 to the controller 42 of the electronic devices 40. Any suitable technique or techniques can be utilized to electrically connect the detector 90 to the conductor 92.

Figure 6:
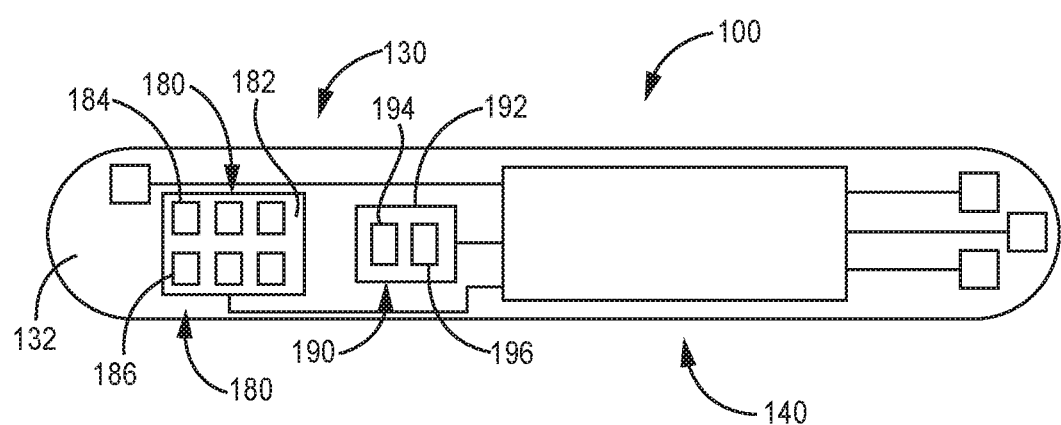
FIG. 6 is a schematic perspective view of a first major surface of a substrate of another embodiment of a sealed package.

As mentioned herein, the package 10 can include any suitable number of light sources 80 and detectors 90. For example, FIG. 6 is a schematic plan view of another embodiment of a sealed package 100. All of the design considerations and possibilities regarding the sealed package 10 of FIGS. 1-5 apply equally to the package 100 of FIG. 6. The package 100 includes a housing (not shown for clarity) and a substrate 130 hermetically sealed to the housing and including a first major surface 132 and a second major surface (not shown). One difference between the package 100 of FIG. 6 and the package 10 of FIGS. 1-5 is that package 100 includes electronic devices 140 that include an array of light sources 180. The array 180 is disposed on a substrate 182. In one or more embodiments, the one or more light sources of the array 180 can be disposed on the substrate 182 or directly onto the first major surface 132 of the substrate 130 of the package 100.

The array 180 can include any suitable number of light sources. In the embodiment illustrated in FIG. 6, the array includes six light sources. Each of the light sources of the array 180 can have the same properties. In one or more embodiments, one or more light sources of the array 180 can have one or more properties that are different from the properties of one or more additional light sources of the array. For example, a first light source 184 of the array 180 can emit light having a first wavelength, and a second light source 186 of the array can emit light having a second wavelength that is the same as or different from the first wavelength. In one or more embodiments, the light sources of the array 180 can be independently addressable such that one or more of the light sources can be turned on or off independent from one or more additional light sources of the array.

Another difference between package 100 and package 10 is that the package 100 includes an array of detectors 190 having, in the illustrated embodiment, a first detector 194 and a second detector 196 disposed on a substrate 192. In one or more embodiments, the detector array 190 can include any suitable number of detectors. The detectors of the array 190 can be disposed on the substrate 192 or directly on the second major surface 132 of the substrate 130. Each of the detectors of the array 190 can be the same; alternatively, at least one detector of the array can be different from another detector of the array. For example, the first detector 194 can be adapted to detect light having a first wavelength, and the second detector 196 can be adapted to detect light having a second wavelength that is the same as or different from the first wavelength. In one or more embodiments, the detectors of the detector array 190 can be independently addressable such that one or more of the detectors can be turned on or off independent from one or more additional detectors of the array.

Returning to FIGS. 1-5, the electronic device 40 can be electrically connected to one or more additional electronic devices disposed on one or both of the first major surface 32 and second major surface 34, or within the housing 20. For example, the electronic devices 40 can be electrically connected to the power source 50 using any suitable technique or techniques. In one or more embodiments, the electronic devices 40 can include one or more device contacts 44 (FIG. 3) that are electrically connected to one or more of the electronic devices using any suitable technique or techniques. Device contacts 44 are electrically connected to one or more devices 40 through conductors 46. Although illustrated as including two device contacts 44, the package 10 can include any suitable number of device contacts. The device contacts 44 can include any suitable contacts, pads, terminals, etc., that provide electrical connection to other devices, e.g., power source 50. The contacts 44 can take any suitable shape or combination of shapes and be disposed in any suitable location on or in the first major surface 32 of the substrate 30. Any suitable technique or techniques can be utilized to form device contacts 44 and conductors 46, e.g., chemical vapor deposition, plasma vapor deposition, physical vapor deposition, etc., followed by photolithography, chemical etching, etc. Further, the device contacts 44 and conductors 46 can include any suitable conductive material or combination of conductive materials. In one or more embodiments, the electronic devices 40 can be electrically connected to other electronic circuitry or devices disposed on or adjacent the substrate 30 or within the housing 20.

The electronic devices 40 can be electrically connected to device contacts 44 and conductors 46, 82, 92 using any suitable technique or techniques. For example, in one or more embodiments, solder bumps and/or contact pads of the electronic devices 40 can be directly attached to one or more contacts 44 using any suitable technique or combination of techniques, e.g., soldering, welding, laser bonding, mechanically connecting (e.g., direct-pressure contacts), etc. In one or more embodiments, one or more conductors 46, 82, 92 can be electrically connected to one or more device contacts 44 and one or more solder bumps and/or contact pads of one or more of the electronic devices 40 using any suitable technique or combination of techniques, e.g., soldering, welding, laser bonding, mechanically connecting (e.g., direct-pressure contacts), etc.

Any suitable technique or techniques can be utilized to dispose the device contacts 44 and the conductors 46, 82, 92 on the substrate 30, e.g., the techniques described in U.S. Patent Publication No. 2016/0185081, entitled KINETICALLY LIMITED NANO-SCALE DIFFUSION BOND STRUCTURES AND METHODS. For example, electromagnetic radiation can be directed through substrate 30 from the second major surface 34 to a region between the device contacts 44 and the substrate 30, and between the conductors 46, 82, 92, and the substrate 30. The electromagnetic radiation can form a bond that seals the device contacts 44 and the conductors 46, 82, 92 to the substrate 30 in any suitable pattern or shape. The bond can be a laser bond.

The package 10 can also include power source 50. Any suitable power source or combination of power sources can be utilized with package 10, e.g., one or more batteries, capacitors, inductive-coupled energy devices, photovoltaic devices, betavoltaic devices, alphavoltaic devices, and thermo-electric devices.

The power source 50 can be disposed in any suitable location. In one or more embodiments, the power source 50 is disposed at least partially within the housing 20. As used herein, the term "at least partially within" means that at least a portion of the power source 50 is disposed within the housing 20. In one or more embodiments, the entire power source 50 can be disposed within the housing 20. The power source 50 can include its own housing or casing. In one or more embodiments, the housing 20 provides at least a portion of an outer casing for the power source 50. For example, the inner surface 22 of the housing 20 can provide a portion of a casing of the power source 50, and a separate cover or protective layer can be disposed within the housing such that the power source is between the protective layer and the inner surface of the housing. The power source 50 can be integral with the housing 20. In one or more embodiments, the power source 50 is a separate element that is separately manufactured and then disposed within the housing 20.

The power source 50 includes one or more power source contacts 52, 54. Although depicted as including three contacts 52, 54 the power source 50 can include any suitable number of contacts that can be electrically connected to one or more devices to provide electrical energy to such devices from the power source. The power source contacts 52, 54 can be disposed in any suitable location relative to the power source 50. As illustrated in FIG. 2, the power source contacts 52, 54 are disposed at a first end 53 of the power source 50.

The power source contacts 52, 54 can include any suitable contact, e.g., the same contacts described regarding device contacts 44. In one or more embodiments, the power source contacts 52, 54 can include one or more compressible or resilient members that can engage one or more device contacts, e.g., device contacts 44, when the substrate 30 is sealed to the housing 20. Each power source contact 52, 54 can be the same contact or type of contact. In one or more embodiments, each power source contact 52, 54 can be different from each additional power source contact.

The electronic devices 40 can, in one or more embodiments, be electrically connected to the power source 50 using any suitable technique or techniques. In one or more embodiments, the one or more of the electronic devices 40 can be electrically connected to the power source 50 when the substrate 30 is sealed to the housing 20. Any suitable technique or techniques can be utilized to electrically connect the electronic devices 40 to the power source 50 when the substrate 30 is sealed to the housing 20. For example, one or more power source contacts 52, 54 can be electrically connected to one or more device contacts 44 when the substrate 30 is sealed to the housing 20. Any suitable electrical coupling between the power source contacts 52, 54 and the device contacts 44 can be utilized. In one or more embodiments, a non-bonded electrical connection can be formed between one or more device contacts 44 and one or more power source contacts 52, 54 when the substrate 30 is sealed to the housing 20. As used herein, the term "non-bonded electrical connection" means that an electrical connection is formed between two or more contacts, terminals, electrodes, etc., that can be maintained by suitable contact pressure between the two or more contacts to maintain the electrical connection, without the use of a bonding agent, e.g., a conductive adhesive, solder, etc. In one or more embodiments, a bonded electrical connection can be formed between one or more device contacts 44 and one or more power source contacts 52, 54 using any suitable technique or combination of techniques.

The substrate 30 can be sealed to the housing 20 using any suitable technique or techniques, e.g., mechanically fastening, adhering, press fitting, laser bonding, magnetic coupling, etc. In one or more embodiments, the first major surface 32 of the substrate 30 can be sealed to an edge surface 29 of a flange 28. The flange 28 can be integral with the housing 20. In one or more embodiments, the flange 28 can be attached to the housing using any suitable technique or techniques.

In one or more embodiments, the substrate 30 can be hermetically sealed to the housing 20. Any suitable technique or techniques can be utilized to hermetically seal the substrate 30 to the housing 20. For example, in one or more embodiments, the substrate 30 can be hermetically sealed to the housing 20 by a bond. Any suitable technique or techniques can be utilized to form such bond, e.g., the techniques described in co-owned and co-filed U.S. Patent Publication No. 2016/0185081, entitled KINETICALLY LIMITED NANO-SCALE DIFFUSION BOND STRUCTURES AND METHODS. In one or more embodiments, electromagnetic radiation (e.g., light) can be directed through substrate 30 from the second major surface 34 and focused at a region between the substrate and the housing 20. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 2000 nm. For example, laser light can include UV light, visible light, IR light, and combinations thereof. The UV light can be provided by a UV laser that has any suitable wavelength or range of wavelengths and any suitable pulse width. In one or more embodiments, a UV laser can be utilized to provide light having a wavelength in a range of 100-400 nm and a pulse width in a range of 1-100 ns. In one or more embodiments, the materials for the substrate 30 and the housing 20, and the power level and wavelength of the light used may be selected such that the light may not directly damage, ablate, warp, or cut the substrate and the housing, and such that the substrate and the housing retain their bulk properties.

In general, light can be provided by any suitable laser or laser system. For example, the laser may generate light having a relatively narrow set of wavelengths (e.g., a single wavelength). In one or more embodiments, the light emitted by the laser may form a collimated beam that may not be focused at a particular point. In one or more embodiments, the light emitted by the laser may be focused at a focal point at a region between the first major surface 32 of the substrate 30 and the housing 20 to generate a laser bond.

Although the laser may provide light that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat, Gaussian, or other suitable spatial energy profile.

As mentioned herein, one or more electronic devices 40 can be disposed on the first major surface 32 of the substrate 30. In one or more embodiments, one or more additional devices or features can also be disposed on the second major surface 34 of the substrate 30. For example, in the embodiment illustrated in FIGS. 1-5, the first electrode 74 and the second electrode 76 are disposed on the second major surface 34 of the substrate 30. The first and second electrodes 74, 76 can include any suitable electrode or combination of electrodes and can take any suitable shape and have any suitable dimensions.

One or both of the first and second electrodes 74, 76 can be utilized to electrically connect the package 10 to any suitable device or devices that are external to the package. For example, one or both of the first and second electrodes 74, 76 can electrically connect the package 10 to a lead of an implantable medical device. In one or more embodiments, one or both of the first and second electrodes 74, 76 can electrically connect the package 10 to one or more additional power sources. Further, in one or more embodiments, one or both of the first and second electrodes 74, 76 can be therapeutic electrodes that can be utilized for delivering and/or receiving one or more electrical signals to or from a patient, either while the package is external or internal to a patient. Any suitable technique or techniques can be utilized to electrically connect the package 10 to one or more devices through one or both of the first electrode 74 and second electrode 76, e.g., soldering, physical contact, welding, etc. The first and second electrodes 74, 76 can include any suitable conductive material or combination of conductive materials, e.g., copper, silver, titanium, niobium, zirconium, tantalum, stainless steel, platinum, iridium, or combinations thereof. In one or more embodiments, the first and second electrodes 74, 76 can include two or more materials, e.g., bi-metals, clad laminates, etc.

Further, the first and second electrodes 74, 76 can take any suitable shape or combination of shapes. In one or more embodiments, the first and second electrodes 74, 76 can take a circular shape in a plane parallel to the second major surface 34 of the substrate 30. In one or more embodiments, the first and second electrodes 74, 76 can take a rectangular shape in the plane parallel to the second major surface 34. Further, the first and second electrodes 74, 76 can take any suitable shape or combination of shapes in a plane orthogonal to the second major surface 34, e.g., square, tapered, domed, etc. In one or more embodiments, the first and second electrodes 74, 76 can include complex shapes such as grooves or channels formed in the electrode to facilitate attachment of conductors or electronic devices to the contacts.

The first and second electrodes 74, 76 can also include any suitable dimensions. In one or more embodiments, the first and second electrodes 74, 76 can have any suitable thickness in a direction normal to the second major surface 34 of the substrate 30. In one or more embodiments, this thickness can be at least 10 micrometers. In one or more embodiments, the thickness can be no greater 200 micrometers. In one or more embodiments, the first and second electrodes 74, 76 can be of sufficient size and thickness to enable laser, resistance, or other welding and joining techniques to be utilized to electrically couple conductors and/or electronic devices to the electrode.

The first and second electrodes 74, 76 can be electrically connected to one or more electronic devices disposed on or within the package, e.g., electronic device 40. Any suitable technique or techniques can be utilized to electrically connect one or both of the first and second electrodes 74, 76 to one or more devices disposed on or within the housing. In one or more embodiments, the first electrode 74 can be electrically connected to device 40 through via 78 (FIG. 3), which is electrically connected to device 40 through conductor 75. Via 78 can be formed between the first major surface 32 and the second major surface 34 of the substrate 30, and a conductive material can be disposed within the via using any suitable technique or combination of techniques. Similarly, second electrode 76 can be electrically connected to electronic device 40 through via 79 (FIG. 3), which is electrically connected to the device through conductor 77.

Once again, via 79 can be formed between the first major surface 32 and the second major surface 34 of substrate 30, and conductive material can be disposed within the via using any suitable technique or combination of techniques.

The package 10 of FIGS. 1-5 can also include the conductor 70 disposed on the second major surface 34 of the substrate 30 or within the substrate between the first major surface 32 and the second major surface 34. The conductor 70 can include any suitable shape or combination of shapes and can be formed using any suitable conductive material. Although depicted as including one conductor 70, two or more conductors can be formed on the second major surface 34 of the substrate 30 or within the substrate. Further, the conductor 70 can be patterned to include any suitable shape or combination of shapes.

In one or more embodiments, the conductor 70 can be formed to provide an antenna, and the package 10 can be wirelessly coupled to a device or system through such antenna. The package 10 can wirelessly communicate through the antenna utilizing, e.g., RF, inductive, optical, magnetic, acoustic, or other transmission mechanisms. Further, in one more embodiments, the conductor 70 can form an inductive coil that can be utilized to provide inductive coupling to one or more external devices, e.g., one or more inductive power sources.

The conductor 70 can be electrically connected to one or more electronic devices disposed within the housing of the package 10 using any suitable technique or techniques. For example, a via (not shown) can be formed between the first major surface 32 and the second major surface 34 of the substrate 30 that is that is electrically connected to, e.g., one or more electronic devices 40 through a conductor. Conductive material can be disposed within the via that electrically connects the conductor 70 to one or more electronic devices 40. The conductor 70 can be electrically connected to the via using any suitable technique or techniques.

The electronic devices 40 can include an accelerometer (not shown) disposed in any suitable location on or within the substrate 30 or housing 20 of the package 10. In one or more embodiments, the accelerometer can be utilized to mitigate potentially confounding influences caused by the motion and/or posture of the patient. A measurement period of the package 10 can be deferred if the accelerometer or other electronic device 40 detects a high activity level of the patient until such time that a low activity level occurs. In one or more embodiments, a measurement period can be deferred until the patient is in a preferred posture.

Likewise, for ambient light, the detector 90 can detect an ambient light level. If the ambient light level is below a selected low level threshold, then measurement of a physiological condition of the patient can proceed. If the level is above the low-level threshold but below an intermediate ambient light threshold, then physiological measurements may proceed. The controller 42 can be adapted to subtract or remove the ambient light level from the measurement. If the ambient light level is above a high ambient light threshold, then the measurement can be deferred until ambient light returns to a level below the intermediate or low ambient light thresholds. The controller 42 can also be adapted to defer measurement based upon other conditions, e.g., temperature, respiration, ECG anomalies, etc. Deferring measurement based upon one or more selected conditions can help to preserve battery power and to capture physiologically meaningful data, e.g., measurement may be activated when a patient is having an ECG episode.

The various embodiments of packages described herein can be utilized to determine one or more physiological conditions. Any suitable physiological condition can be determined, e.g., heart rate, arterial blood oxygen level ($SpO_2$), blood flow, fluid volume (e.g., edema), tissue oxygen saturation ($StO_2$), perfusion index (PI), Total Hemoglobin/Hematocrit, Tissue Hemoglobin Concentration Index (THI), venous oxygen saturation ($SvO_2$), ambient light level within a patient, respiration rate, optically interrogated biochemical sensors (e.g., fluorescent or other coatings and materials in contact with tissue), pulse wave velocity (e.g., pulse transit time), etc.

Figure 7:
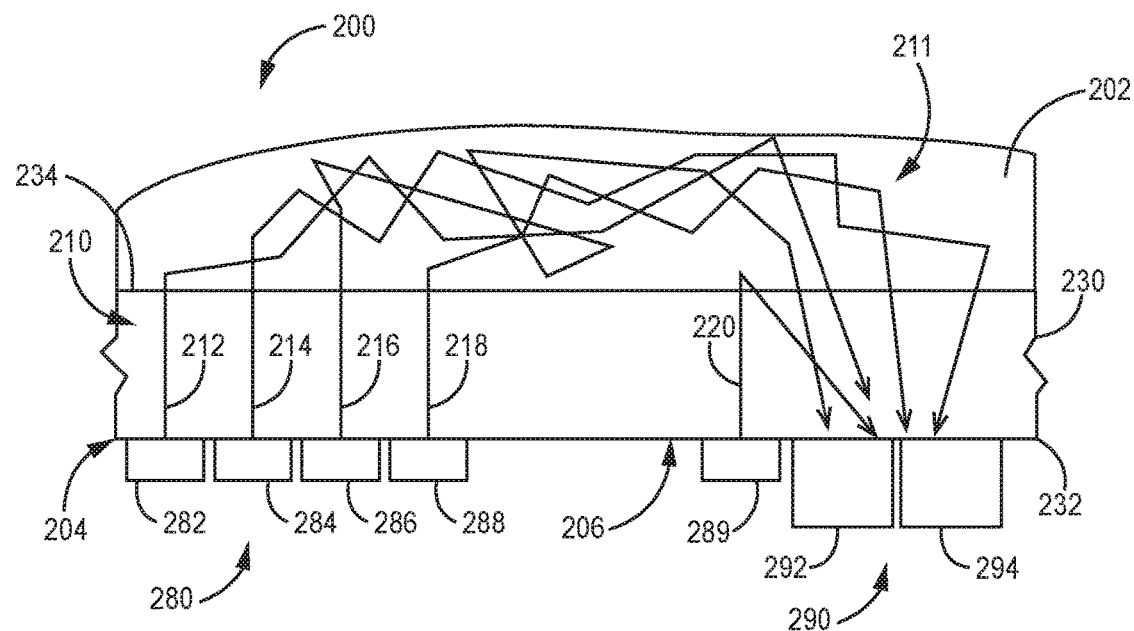
FIG. 7 is a schematic cross-section view of another embodiment of a sealed package disposed within a patient and adjacent tissue of the patient.

For example, FIG. 7 is a schematic cross-section view of a portion of one embodiment of a sealed package 200 implanted within a patient adjacent or within tissue 202. All of the design considerations and possibilities regarding the package 10 of FIGS. 1-5 apply equally to the package 200 of FIG. 7. The package 200 includes a housing (not shown for clarity) and a substrate 230 sealed to the housing. Light source array 280 is disposed on a first portion 204 of a first major surface 232 of the substrate 230 and includes a first light source 282, a second light source 284, a third light source 286 and a fourth light source 288. The light source array 280 further includes a fifth light source 289 disposed on a second portion 206 of the first major surface 232 of the substrate 230. Each of the light sources of the array 280 is adapted to emit light 210 through the first major surface 232 and a second major surface 234 of the substrate 230.

The package 200 also includes a detector array 290 that includes a first detector 292 and a second detector 294 each disposed on the first major surface 232 of the substrate 230. Each detector of the detector array 290 is adapted to detect at least a portion of the light 210 emitted by the light source array 280.

Light 210 emitted from the light source array 280 is scattered and absorbed by the body fluid or tissue volume 202. At least a portion of light 211 that is scattered by the volume 202 travels through the substrate 230 to the detector array 290. Scattered light that corresponds to wavelengths to which the detector array 290 is responsive will cause one or both of the detectors 292, 294 to generate current or voltage corresponding to various characteristics (e.g., intensity) of the detected light. Light modulation due to a physiological change may result in a signal generated by the detector array 290 that may be correlated to a changing physiological condition.

Each light source of the light source array 280 can be adapted to emit light having a selected characteristic. For example, light source 282 can be adapted to emit light 212 having a first wavelength, light source 284 can be adapted to emit light 214 having a second wavelength, light source 286 can be adapted to emit light 216 having a third wavelength, and light source 286 can be adapted to emit light 218 having a fourth wavelength. Further, light source 289 can be adapted to emit light 220 having a fifth wavelength. The light emitted by each of the light sources of the array 280 can have the same wavelength or different wavelengths as the light emitted by one or more of the other light sources of the array.

Similarly, the various detectors of the detector array 290 can each be adapted to detect light having a selected characteristic (e.g., wavelength). For example, detector 292 can be adapted to detect light 212, 218, and 220 that has been emitted by light sources 282, 288, and 289 and scattered by volume 202. Further, detector 294 can be adapted to detector light 214 and 216 emitted by light sources 284 and 286.

As such, light scattered by body fluid or tissue volume 202 can cause the detector array 290 responsive to selected light wavelengths to emit a signal useful in measurement of one or more physiological conditions (or changes in such physiological conditions) in the body fluid or tissue volume. For example, the light source array 280 and detector array 290 can be adapted to estimate oxygen saturation in blood. In such an embodiment, one or more light sources of the light source array 280 can be adapted to emit red light. The intensity of red light scattered by the body fluid or tissue volume 202 and detected by detector array 290 is dependent on the concentration of oxygenated hemoglobin in the blood. The intensity of infrared light scattered by the body fluid or tissue volume 202 can be made independent of the concentration of oxygenated hemoglobin by proper choice of wavelength (e.g., 800 nm). The scattered red light detected can be normalized by the infrared light detected to correct for variables such as total hemoglobin, tissue overgrowth, and blood flow velocity or other artifacts.

Figure 8:
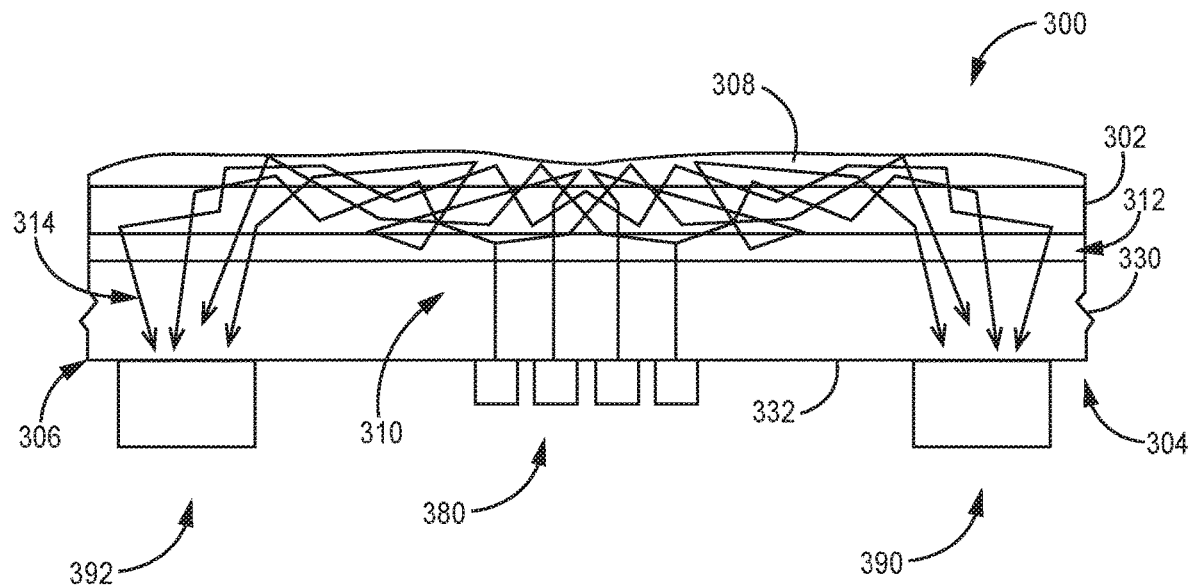
FIG. 8 is a schematic cross-section view of another embodiment of a sealed package disposed within a patient and adjacent an artery of the patient.

In one or more embodiments, a sealed package described herein can measure pulse wave velocity of blood flow of a patient. For example, FIG. 8 is a schematic cross-section view of a portion of another embodiment of a sealed package 300 implanted within a patient adjacent an artery 302. All of the design considerations and possibilities regarding the sealed package 10 of FIGS. 1-5 apply equally to the sealed package 300 of FIG. 8. The package 300 includes a housing (not shown for sake of clarity) and a substrate 330 sealed to the housing. The package 300 also includes a light source array 380 disposed on a first major surface 332 of the substrate 330. The package 300 further includes a first detector 390 disposed on a first portion 304 of the first major surface 332 of the substrate 330, and a second detector 392 disposed on a second portion 306 of the first major surface of the substrate.

The light source array 380 can be adapted to emit light of any suitable wavelength or wavelengths. In one or more embodiments, each light source of the array 380 can emit the same wavelength as one or more additional light sources or different wavelengths. Further, the detectors 390, 392 can be adapted to detect any suitable wavelength or wavelengths.

In general, the package 300 can be disposed adjacent or in contact with the artery 302 such that at least a portion of light 310 emitted by one or more of the light sources 380 is incident upon the artery. A first portion 312 of the emitted light 310 is incident upon the artery 302 and is scattered by the artery and surrounding tissue 308. At least a portion of the first portion 312 of light is incident upon the first detector 390, which detects the portion and sends a first signal to a controller or other electronic device (e.g., controller 42 of FIG. 1) disposed within the housing of the package 300. Further, a second portion 314 of light is emitted by the light sources 380 and incident upon the artery 302, where it is scattered by the artery and surrounding tissue 308. At least a portion of the second portion 314 of light is incident upon the second detector 392, which detects the portion of light and sends a second signal to the controller.

Any suitable technique can be utilized to determine the pulse wave velocity of blood flowing through the artery 302 based upon the first signal and second signal. For example, ECG and single pulsatile optical signal (photoplethysmography PPG) can be simultaneously measured in time sync. The R wave from the ECG signal can be detected and marked. A fiducial on the PPG such as peak amplitude or initial onset of the systolic response can also be marked. The time interval between the occurrence of the R wave and the PPG fiducial can be measured to determine a pulse transit time. The pulse wave velocity can be calculated based upon the pulse transit time using any suitable technique or techniques.

Further, for example, pulse velocity may be derived by measuring the time between two PPG events utilizing two or more sensors disposed in different positions within the package 300. A fiducial can be applied to each wave form. And the time delay between the two wave forms can be measured to determine pulse velocity.

Figure 9:
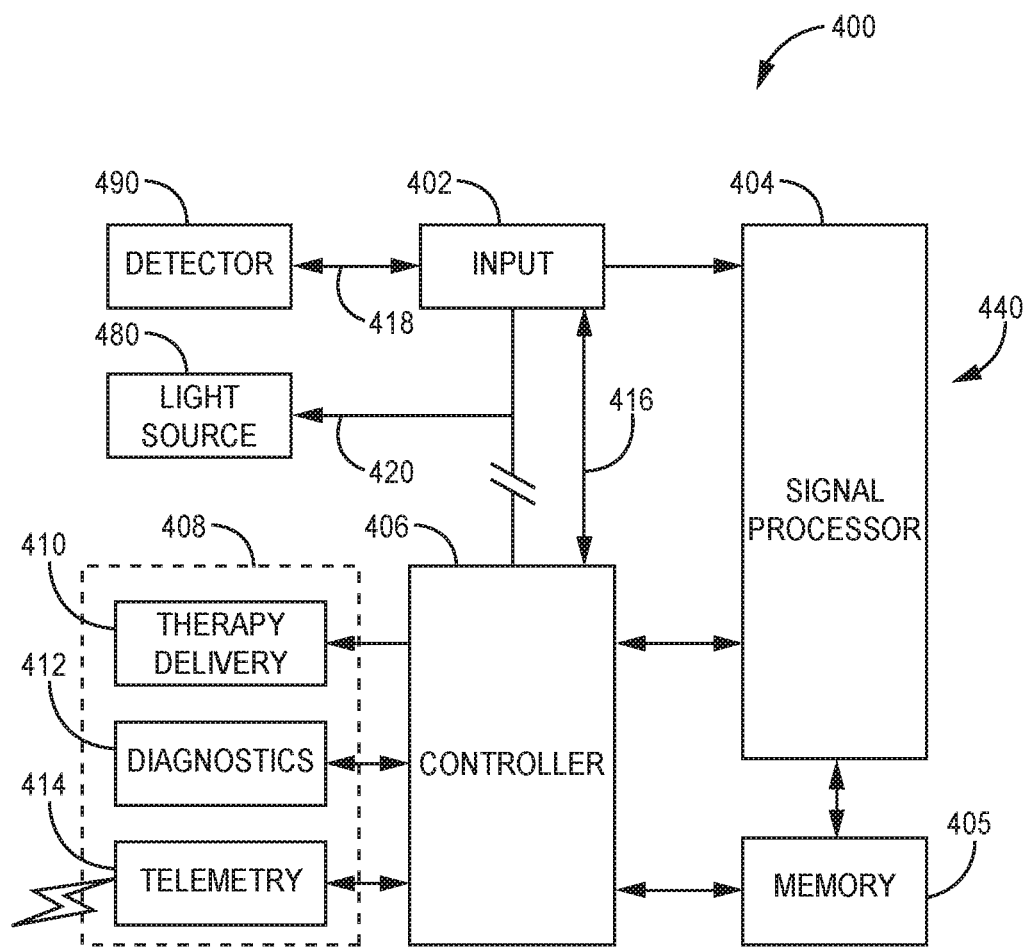
FIG. 9 is a schematic diagram of another embodiment of a sealed package.

Any suitable circuitry or components can be utilized with the various embodiments of sealed packages described herein to provide information regarding a physiological condition or conditions of a patient. For example, FIG. 9 is a schematic block diagram of one embodiment of another embodiment of a sealed package 400. All of the design considerations and possibilities regarding the sealed package 10 of FIGS. 1-5 apply equally to the sealed package 400 FIG. 9. The package 400 includes a housing and a substrate (neither shown for sake of clarity). The package 400 also includes a light source 480 and a detector 490 each disposed on a first major surface of the substrate as is further described herein.

Sealed package 400 can include one or more electronic devices 440 (including the light source 480 and the detector 490) disposed on one or both of a first major surface and a second major surface of the substrate or within the housing (e.g., electronic devices 40 of FIGS. 1-5). In addition to the light source 480 and the detector 490, the electronic devices 440 include an input module 402, signal processor 404, memory 405, controller 406, and output module 408.

Input module 402 receives one or more signals when enabled for sensing by controller 406 by control/status line 416. Input module 402 may perform pre-processing signal conditioning, such as analog filtering. Input module 402 selects the functionality of the light source 480 and the detector 490 via control bus 418 and 420 under the control of controller 406. Input module 402 further provides one or more signals from detector 490 to signal processor 404. Input module 402 may additionally provide other sensor signals to processor 404 and/or controller 406 for use in monitoring physiological signals and detecting physiological conditions or events.

The techniques employed for controlling the light source 480 and the detector 490 will depend in part on the overall medical device architecture and hardware, firmware, and software employed. In one or more embodiments where the light source 480 includes multiple light sources and the detector 490 includes multiple detectors, selection of a light source and detector to operate includes providing a control signal on control bus 418 for coupling the detector 490 to a photo-integrator that converts the device-generated current to a voltage signal, which is then provided to an A/D converter. Selection of a light source 480 generally includes coupling the source to a drive signal source to activate the light source to emit light. One example of a bus system for controlling a device is generally disclosed in U.S. Pat. No. 7,013,178 (Reinke, et al.).

Processor 404 receives the signals from the detector 490 and performs signal processing to provide controller 406 with signals useful in monitoring a patient condition and appropriately control output module 408. Processor 404 may be a digital signal processor (DSP), analog processor, or a combination of both analog and digital processors.

Controller 406 controls input module 402 to select the functionality of the light source 480 and detector 490 during a performance test. The sealed package 400 can execute an optical sensor performance test to evaluate optical sensor signals obtained during different assembly functionality configurations. The functional configuration of the light source 480 and the detector 490 are controlled by the controller 406. The controller 406 controls the selection of each assembly to function as either a light emitting portion or a light detecting portion (or neither or both light emitting and light detecting in some embodiments) in a functional configuration of the light source 480 and detector 490 used for patient monitoring.

During a performance test, functionality of the light source 480 and detector 490 are controlled and detector signals are provided to processor 404. Processor 404 provides the controller 406 signal data from which controller 406 determines the optimal assembly functionality configuration for optical sensing. The optimal sensing configuration is then selected by input module 402 under the control of controller 406 during episodes in which the light source 480 and detector 490 are enabled for monitoring physiological signals.

Signal data may be stored in memory 405 by processor 404 and retrieved by controller 406 for use in determining an optimal functional configuration of the light source 480 and detector 490. Algorithms for a performance test and other functions may also be stored in memory 405 and retrieved by controller 406.

During normal operation, controller 406 analyzes processed signals provided by processor 404 to detect physiological events or patient conditions. Controller 406 can determine which emitting and detecting configurations of the light source 480 and detector 490 provide signals with the highest signal-to-noise ratio and acceptable signal level and may select additional light sources, detectors, and other types of sensors (e.g., an accelerometer) to operate to provide redundant signals to promote accurate detection. In one or more embodiments, controller 406 may select emitting and detecting configurations of one or both of the light source 480 and sensor 490 that minimize energy demands while providing a reliable sensor signal for use in patient monitoring. The ability to select the functionality of one or both of the light source 480 and sensor 490 over time allows the sealed package 400 to accommodate situations in which signal characteristics change over time, for example, due to shifting of the package or changes in adjacent tissue composition such as increased tissue encapsulation. By periodically repeating performance tests, controller 406 can select the optimal configuration light sources and detectors as it changes over time.

Controller 406 uses the digitally processed signals to make decisions regarding therapy delivery by therapy delivery module 410, for determining and storing a diagnostic output (such as a detected physiological event) in diagnostics module 412, and/or for selecting data to be transmitted by telemetry module 414. Controller 406 may employ a microprocessor and associated memory 405 or digital state machines for timing sensing and therapy delivery functions and controlling other device operations in accordance with a programmed operating mode. The signal acquisition, processing and analysis methods described herein and selection of one or more light sources and detectors may be implemented using any combination of software, hardware, and/or firmware.

Therapy delivery module 410 may provide electrical stimulation therapy or drug delivery therapy. In one or more embodiments, therapy delivery module 410 includes a pulse generator for generating low-voltage pacing pulses, e.g., for bradycardia pacing, cardiac resynchronization therapy, and anti-tachycardia pacing. Therapy delivery module 410 may further include high-voltage circuitry for generating high-voltage cardioversion/defibrillation shocks. Therapy delivery unit 410 includes therapy delivery elements (not explicitly shown) such as electrodes, catheters, drug delivery ports or the like for administering a therapy.

Diagnostics module 412 may be used to detect a physiological event or patient condition using any available sensor signals or other data acquired by the IMD and store data relating to the analysis of processed signals. Stored data may be made available to a clinician through telemetry by telemetry module 414 or accessed by controller 406 for making therapy decisions.

Figure 10:
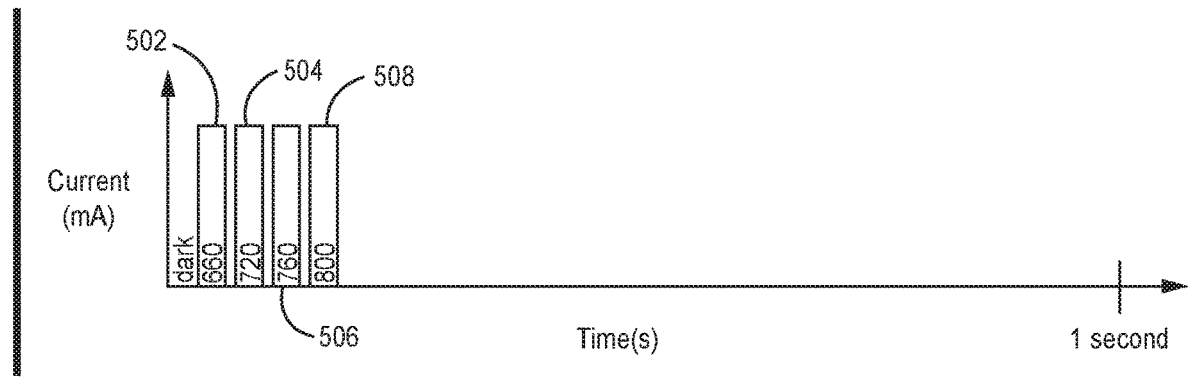
FIG. 10 is a graph of current versus time for one embodiment of a detection method.
Figure 11:
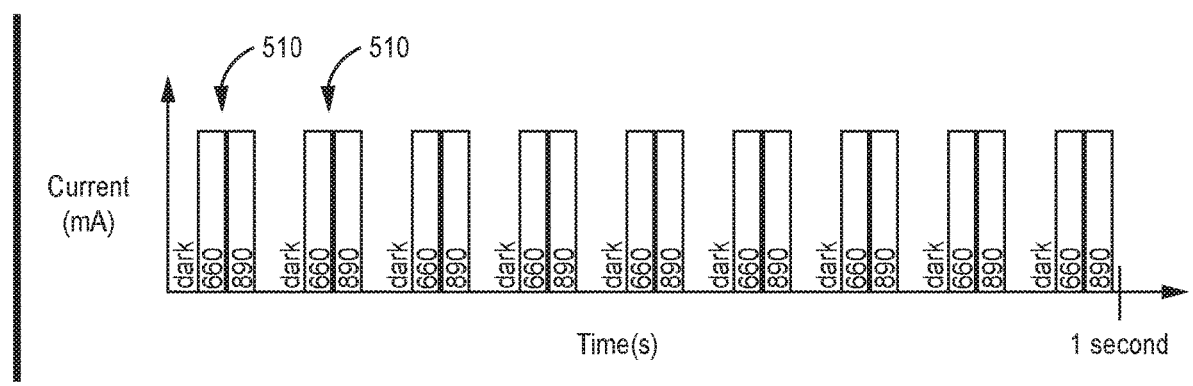
FIG. 11 is a graph of current versus time for another embodiment of a detection method.

The controller 406 can be adapted to control the light source 480 and detector 490 in any suitable manner to detect any desired physiological condition of a patient. For example, FIG. 10 is a graph of current (mA) versus time (s) for one technique for measuring a blood oxygen level ($StO_2$) of a patient. The controller 406 can be adapted to direct a first light source to emit a light pulse 502 at a first wavelength (e.g., 660 nm) and a second light source to then emit a second light pulse 504 at a second wavelength (e.g., 720 nm). The process is repeated with a third light pulse 506 at the first wavelength followed by a fourth light pulse 508 at the second wavelength. A first waveform can be detected and a second waveform can be interpolated based upon the timing of the first waveform to yield an approximation of concurrent events Further, for example, FIG. 11 is a graph of current (mA) versus time (s) for a technique for measuring arterial oxygen saturation ($SpO_2$) of a patient. The controller 406 can be adapted to direct first and second light sources to emit one or more light pulses 510 that include a first wavelength (e.g., 660 nm) followed by a second wavelength (890 nm). Any suitable number of pulses can be directed to tissue of a patient to determine the arterial oxygen saturation.

Figure 12:
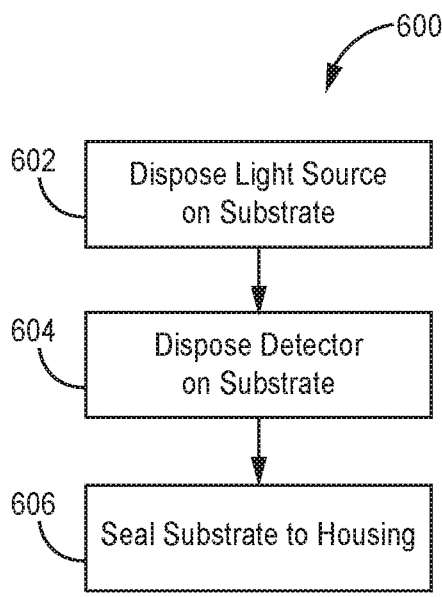
FIG. 12 is a flow chart of one embodiment of a method of forming a sealed package.

The sealed packages described herein can be manufactured using any suitable technique or combination of techniques, e.g., the techniques described in co-owned U.S. Patent Application No. 62/250,194, filed Nov. 3, 2015, and entitled SEALED PACKAGE INCLUDING ELECTRONIC DEVICE AND POWER SOURCE. For example, FIG. 12 is a flowchart of one method 600 of forming a sealed package. Although method 600 can be utilized to form any sealed package, the method will be described in reference to package 10 of FIGS. 1-5. The method 600 includes disposing the light source 80 on the substrate 30 (or within the housing 20) at 602 using any suitable technique or techniques. The detector 90 can also be disposed on the substrate 30 (or within the housing 20) at 604 using any suitable technique or techniques. In one or more embodiments, one or more additional electronic devices 40 can be disposed on the substrate 30 (or within the housing 20) using any suitable technique or techniques, e.g., controller 42. The substrate 30 can be sealed to the housing 20 at 606 using any suitable technique or techniques, e.g., either the first or second major surface 32, 34 of the substrate can be laser bonded to the housing 20. In one or more embodiments, the substrate 30 can be hermetically sealed to the housing 20. In one or more embodiments, one or more additional devices or components (e.g., conductor 70, electrodes 74, 76) can be disposed on the second major surface 34 of the substrate 30 either before or after the substrate is sealed to the housing 20 using any suitable technique or techniques.

Figure 13:
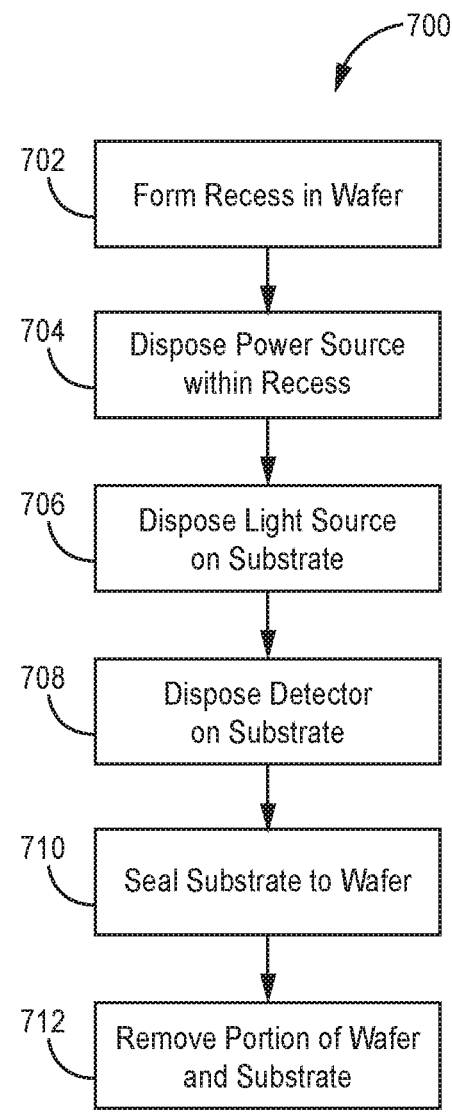
FIG. 13 is a flow chart of another embodiment of forming a sealed package.

Further, for example, FIG. 13 is a flow chart of another embodiment of a method 700 for forming a sealed package, e.g., package 10 of FIGS. 1-5. A housing wafer can be provided, and one or more recesses can be formed in the wafer at 702. The housing wafer can include any suitable material or combination of materials, e.g., the same materials described regarding housing 20 of FIG. 1. One or more power sources 50 can each be disposed within one or more of the recesses formed in the wafer at 704 using any suitable technique or techniques. In one or more embodiments, the power source 50 can be formed separately and then disposed within the recess. In one or more embodiments, the power source 50 can be formed within the recess using any suitable technique.

Further, at 706, one or more electronic devices 40 can be disposed on a major surface of the substrate 30, e.g., on the first major surface 32 of the substrate. In one or more embodiments, a plurality of devices can be disposed on a substrate wafer that are registered or aligned with the power sources 50 and the recesses. One or more detectors 90 can be disposed on the first major surface 32 of the substrate 30 or within the recesses at 708. At 710, the major surface of the substrate 30 can be sealed to the wafer using any suitable technique or techniques, e.g., the substrate can be sealed to the wafer using laser bonding. At 710, a portion of the wafer and the substrate 30 can be removed to form the sealed package or packages, e.g., a plurality of sealed packages can be singulated from the housing wafer and substrate. Any suitable technique or techniques can be utilized to remove portions of the wafer and substrate, e.g., laser cutting, mechanical cutting, etching, etc.

Figure 14:
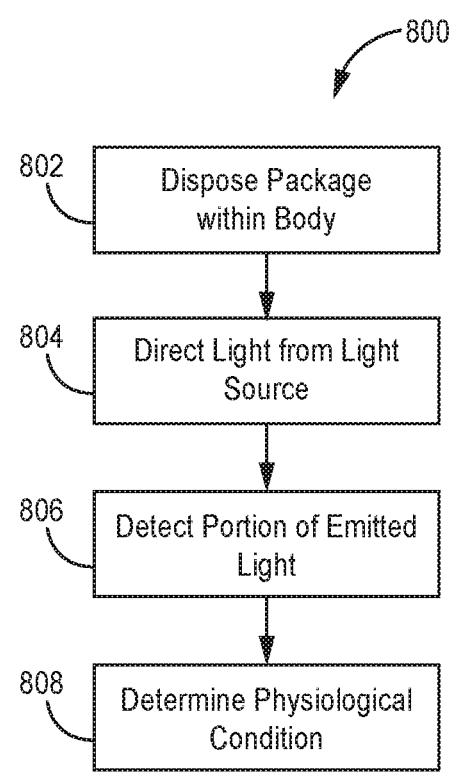
FIG. 14 is a flow chart of one embodiment of a method of detecting a physiological condition utilizing a sealed package disposed within a patient.

The various embodiments of sealed packages described herein can be utilized with any technique or combination of techniques to determine a characteristic or physiological condition of a patient. For example, FIG. 14 is a flowchart of one embodiment of a method 800 of detecting a physiological condition or characteristic of a patient. The method 800 can be utilized to detect any desired physiological condition or characteristic, e.g., blood oxygen level of the patient.

The method 800 includes disposing a hermetically sealed package within a body of the patient at 802. Any suitable hermetically sealed package can be utilized with method 800, e.g., sealed package 10 of FIGS. 1-5. Although method 800 is described regarding the package 10 of FIGS. 1-5, the method can be utilized with any suitable sealed package. At 804, light from the light source 80 can be directed such that it is incident upon one or both of tissue or an artery, other desired physiological location of the patient. Any suitable wavelength or wavelengths of light can be emitted by the light source 80 and directed to a desired location. At 806, a portion of the light emitted by the light source 80 and scattered by one or both of tissue and the artery of the patient can be detected utilizing the detector 90. The physiological condition of the patient can be determined based upon a characteristic of the detected light at 808 using any suitable technique or techniques. In one or more embodiments, a therapy can be delivered to the patient based upon the detected physiological condition. Any suitable therapy or combination of therapies can be delivered to the patient.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed package, comprising:
   a housing comprising an inner surface and an outer surface;
   a non-conductive substrate comprising a first major surface and a second major surface, wherein the first major surface is hermetically sealed to the housing by a laser bond;
   a light source disposed on the first major surface of the substrate and adapted to emit light through the first and second major surfaces of the substrate; and
   a detector disposed on the first major surface of the substrate and adapted to detect the light emitted by the light source.

2. The package of claim 1, wherein the first major surface of the substrate faces the inner surface of the housing.

3. The package of claim 1, further comprising an antenna disposed on the second major surface of the substrate.

4. The package of claim 1, wherein the light source comprises a light emitting diode (LED).

5. The package of claim 1, wherein the light source comprises a vertical-cavity surface-emitting laser (VCSEL).

6. The package of claim 1, wherein the detector comprises a photodiode.

7. The package of claim 1, wherein the substrate is substantially transmissive to light having a wavelength of at least 200 nm and no greater than 2000 nm.

8. The package of claim 1, wherein the substrate comprises sapphire.

9. The package of claim 1, further comprising a conductor disposed on the first major surface of the substrate, wherein the light source is electrically connected to the conductor.

10. The package of claim 1, further comprising an electronic device disposed on the first major surface of the substrate, wherein at least one of the light source and the detector is electrically connected to the electronic device.

11. The package of claim 10, wherein the electronic device comprises a controller.

12. The package of claim 10, wherein the electronic device comprises a multiplexer.

13. The package of claim 1, further comprising a power source disposed within the housing and electrically connected to the light source and the detector.

14. The package of claim 1, wherein the light source comprises an emitting surface disposed on the first major surface of the substrate.

15. The package of claim 1, wherein the detector comprises a detecting surface disposed on the first major surface of the substrate.

16. The package of claim 1, wherein the light source is adapted to emit light comprising a first wavelength, wherein the package further comprises a second light source disposed on the first major surface of the substrate that is adapted to emit light comprising a second wavelength, wherein the first wavelength is different from the second wavelength.

17. The package of claim 1, further comprising an accelerometer disposed within the housing.

\* \* \* \* \*